United States Patent [19]

Gregory

[11] 4,036,902

[45] July 19, 1977

[54] CHEMICAL PROCESS PRODUCING AROMATIC HYDROCARBONS BY DEHYDROCYCLODIMERIZATION OF A $C_4$ FEEDSTOCK

[75] Inventor: Reginald Gregory, Camberley, England

[73] Assignee: The British Petroleum Company Limited, London, England

[21] Appl. No.: 696,573

[22] Filed: June 16, 1976

[30] Foreign Application Priority Data

June 23, 1975 United Kingdom ............... 26528/75

[51] Int. Cl.$^2$ ................................................ C07C 3/04
[52] U.S. Cl. ...................................... 260/673; 208/66; 208/135; 208/141; 252/463; 252/475; 260/683.3

[58] Field of Search .................. 260/673; 208/66, 135, 208/141

[56] References Cited

U.S. PATENT DOCUMENTS

| | | |
|---|---|---|
| 3,005,855 | 10/1961 | Keller et al. .......................... 260/673 |
| 3,644,550 | 2/1972 | Beuther et al. ....................... 260/673 |
| 3,830,866 | 8/1974 | D'Allessandro et al. ............ 260/673 |

*Primary Examiner*—Delbert E. Gantz
*Assistant Examiner*—G. E. Schmitkons
*Attorney, Agent, or Firm*—Brooks, Haidt, Haffner & Delahunty

[57] ABSTRACT

This invention relates to a process for producing aromatic hydrocarbons, particularly xylenes, by dehydrocyclodimerization of a $C_4$ feedstock in the presence of a catalyst comprising alumina promoted by zinc or a zinc compound.

8 Claims, No Drawings

CHEMICAL PROCESS PRODUCING AROMATIC HYDROCARBONS BY DEHYDROCYCLODIMERIZATION OF A $C_4$ FEEDSTOCK

The present invention relates to a process for dehydrocyclodimerisation of $C_4$ feedstock to aromatic hydrocarbons, especially xylenes.

It has been known to use synthetic zeolites and/or aluminas as catalysts in the production of aromatics from open chain hydrocarbons. However, the yield of aromatics, and selectivity to xylene in particular, using such catalysts have been unsatisfactory from such hydrocarbons.

It has now been found that by incorporating a catalyst promoter, the activity of conventional catalysts may be increased significantly and improved yields of xylenes may be obtained.

Accordingly, the present invention is a process for producing aromatic hydrocarbons comprising subjecting a $C_4$ feedstock as hereinafter defined to dehydrocyclodimerisation in the presence of a catalyst composition an alumina promoted by zinc or a compound of zinc.

By $C_4$ feedstock is meant here and throughout the specification feedstock containing a single $C_4$ component or mixtures of saturated and/or unsaturated $C_4$ hydrocarbons. Although the presence of isobutene in the feedstock would be preferable, it is not an essential component.

In the catalyst composition of the present invention zinc may be present as such or in the form of a compound. Preferred examples of zinc compounds are zinc oxide and zinc sulphate.

The amount of zinc present in such catalyst compositions may vary between 0.1% and 10%, preferably between 2.5% and 7% by weight of the total alumina in the catalyst composition.

The alumina used in the catalyst composition may be any of the conventional types such as eta-alumina, gamma-alumina, boehmite etc., eta-alumina and boehmite being most preferred.

The catalyst composition is prepared by impregnating the alumina with an aqueous solution of a soluble zinc compound, e.g. zinc nitrate. The paste so formed may be evaporated to dryness under vacuum and then pyrolysed at elevated temperature in a stream of air The catalyst so prepared may be formed as a fixed bed and activated in the reactor tube itself. The activation is carried out by passing air over the catalyst at the proposed reaction temperature.

The $C_4$ feedstock as hereinbefore described is thereafter passed over the catalyst at a temperature between 450° and 700° C, preferably between 500° and 600° C in an inert atmosphere. The inert atmosphere may be provided by a gas inert under the reaction conditions such as nitrogen. Pressures of up to 20 atmosphere may be used for the reaction. The products of the reaction are then identified and isolated.

The invention is further illustrated with reference to the accompanying Examples:

Preparation of 6% ZnO Eta-alumina Catalyst 6.82g of $Zn(NO_3)_2.6H_2O$ was dissolved in about 10 ml distilled water and 22.18g of eta-alumina was added to this solution and the mixture made into a paste with thorough stirring. It was evaporated to dryness in a vacuum over at 120° overnight. The $Zn(NO_3)_2.6H_2O$ was converted to ZnO by heating at 550° in a stream of air for 4 hr.

EXAMPLE 1

The catalyst was activated in situ in a glass tube, flushed with nitrogen, then isobutene was passed over the catalyst at a residence time of 6 sec. at a reaction temperature of 550°. After 1.5 min. on stream 87.6% of the isobutene was converted to give products which expressed as a weight % yield were; other $C_4$ olefins 13.3%, $C_1$ to $C_3$ 28.0%, total aromatics 40.3% of which xylenes made up 19.1%. With a $C_4$ olefin recycle, aromatics were made at a selectivity of 54%.

EXAMPLE 2

The 6% ZnO/Eta-alumina catalyst was reactivated in situ in a stream of air at 550° for 4 hr, flushed with nitrogen, and butadiene raffinate (consisting of propane 0.5, isobutane 1.6, n-butane 3.5, butene-1 1.8, isobutene 67.4, trans-butene-2 17.4 and cis-butene-2 7.8% wt) was passed over the catalyst at a residence time of 6 sec and a reaction temperature of 550°. After 1.5 min on stream 60.8% of the mixed $C_{4s}$ were converted to give products which expressed as a weight % yield were $C_{4s}$ 39.2%, $C_1$ to $C_3$ 18.2%, total aromatics 33.7% of which xylenes made up 19.0%. With a $C_4$ stream recycle, aromatics were made at a selectivity of 55.4% I claim:

1. A process for producing aromatic hydrocarbons comprising subjecting a $C_4$ feedstock to dehydrocyclodimerisation at a temperature between about 450° to 700° C in the presence of a catalyst comprising an alumina promoted by zinc or a compound of zinc.

2. A process according to claim 1 wherein the compound of zinc is zinc oxide or zinc sulphate.

3. A process according to claim 1 wherein the amount of zinc present in the catalyst composition is between 0.1 and 10% by weight of the alumina.

4. A process according to claim 3 wherein the amount of zinc present in the catalyst composition is between 2.5 and 7.0% by weight of the alumina.

5. A process according to claim 1 wherein the alumina is selected from eta-alumina, gamma-alumina and boehmite.

6. A process according to claim 1 wherein the $C_4$ feedstock is passed over the catalyst composition at a temperature between 500° and 600° C.

7. A process according to claim 1 wherein the dehydrocyclo- dimerisation of $C_4$ feedstock is carried out in an atmosphere which is inert under the reaction conditions.

8. A process according to claim 7 wherein the dehydrocyclodimerisation is carried out in an atmosphere of nitrogen.

* * * * *